United States Patent [19]

Andersen et al.

[11] 4,160,714
[45] Jul. 10, 1979

[54] MEASURING CHAMBER UNIT

[75] Inventors: Jørgen Andersen; Ole Nielsen, both of Herlev, Denmark

[73] Assignee: Radiometer A/S, Denmark

[21] Appl. No.: 898,933

[22] Filed: Apr. 21, 1978

Related U.S. Application Data

[63] Continuation-in-part of Ser. No. 732,340, Oct. 14, 1976, abandoned.

[30] Foreign Application Priority Data

Oct. 15, 1975 [DK] Denmark .................. 4645/75

[51] Int. Cl.² ........................................... G01N 27/28
[52] U.S. Cl. .................................. 204/195 R; 73/53; 204/195 M; 204/195 P
[58] Field of Search .............. 204/195; 73/19, 53, 73/64.1, 64.2, 64.3; 324/30 R; 128/2 E, 2 G, 2.1 E

[56] References Cited

U.S. PATENT DOCUMENTS

| | | | |
|---|---|---|---|
| 3,661,010 | 5/1972 | Neuwelt | 73/61 R |
| 3,915,720 | 10/1975 | Tarcza | 106/39.6 |
| 3,997,420 | 12/1976 | Buzza | 204/195 P |

Primary Examiner—G. L. Kaplan
Attorney, Agent, or Firm—Robert E. Burns; Emmanuel J. Lobato; Bruce L. Adams

[57] ABSTRACT

A block-shaped measuring chamber unit, especially for use in electrochemical measuring apparatuses for defining measuring chambers therein. The block-shaped unit has oppositely directed or otherwise differently orientated surface parts each defining a depression to be used as a measuring chamber. These depressions are interconnected by means of straight bores or passages extending through the block-shaped unit. The block-shaped unit is preferably made from machinable glass-ceramic.

14 Claims, 4 Drawing Figures

MEASURING CHAMBER UNIT

REFERENCE TO PRIOR APPLICATION

This application is a continuation-in-part of application Ser. No. 732,340 filed Oct. 14, 1976 and now abandoned.

BACKGROUND OF THE INVENTION

1. Field of the Invention

The present invention relates to a block-shaped measuring chamber unit defining one or more interconnected depressions. Such unit may, for example, be used in electrochemical measuring devices in which case measuring instruments may be sealed to the unit for closing the depressions so as to form measuring chambers.

2. Description of the Prior Art

Electrochemical measuring devices or apparatuses of the type adapted to make a number of different measurements simultaneously or successively in a corresponding number of communicating measuring chambers defined in a measuring chamber unit, are known. In cases where the measuring apparatus or device should be able to make very accurate measurements on a very small liquid or fluid sample, heavy demands must be made on the measuring chambers and the interconnecting passages. Whether the fluid sample on which the measurements should be made is in the form of gas or liquid (which possibly contains dissolved gas) the inner surfaces defining the measuring chambers and the interconnecting passages must be of such a nature that they do not change the composition or characteristics of the fluid sample to any substantial degree when the sample is passed through the measuring chamber unit. Such a change of the composition of the fluid sample may for example be caused by contamination with substances retained in the measuring chambers under a preceding measuring procedure, by absorption of gas from the walls of the measuring chambers into the fluid sample, or by absorption of gas given off from the fluid sample and absorbed by the walls of the measuring chambers. For the reasons stated above it is desirable to make measuring chamber units of the type in question from a material having a high surface density and being inert to the fluid sample, for example stainless steel or glass. However, when these materials are used it is necessary to finish the surfaces of the measuring chambers and the connecting passages by grinding or polishing. Normally, the measuring chambers as well as the interconnecting passages have very small dimensions and are of relatively complex shapes, and therefore, the production of such a measuring chamber unit from glass, stainless steel, or a similar material is relatively expensive. In order to reduce costs it has often been found necessary to make the measuring chamber unit from plastic even though that material is less suitable and in some cases changes the composition of a fluid sample introduced into the measuring chamber unit to such an extent that the error of measurement introduced must be compensated for, if possible.

U.S. Pat. No. 3,997,420 discloses a measuring chamber unit having measuring chambers defined by a number of mutually spaced depressions formed in the same flat surface of a block-shaped body, and adjacent depressions are interconnected by means of V-shaped connecting passages. Such V-shaped passages are disadvantageous because residues of a sample on which measurement is made, is liable to deposit at the bottom of the "V". Furthermore, the V-shaped passages are extremely difficult to clean between successive measurements so that a sample of which measurements are to be made may be contaminated by residues of a preceding sample. U.S. Pat. No. 3,661,010 discloses an analyzing apparatus in which oppositely directed measuring instruments are arranged at opposite ends of a single through-going, cylindrical measuring chamber provided with inlet and outlet passages extending at right angles to the axis of the cylindrical measuring chamber. This known principle may only be used for an equal number of measuring chambers, and in order to obtain a desired small volume of each measuring chamber the spacing between the oppositely arranged measuring instruments must be relatively small. Furthermore, the shape of the measuring chamber is to a high extent determined by the shapes of the oppositely arranged active surface parts of the measuring instruments. These facts severely limit the freedom of choice of a designer constructing an analyzing apparatus including the measuring chamber unit.

SUMMARY OF THE INVENTION

The present invention provides a measuring chamber unit which is simple to produce and wherein the surfaces of the measuring chambers as well as of their interconnecting passages are simple to finish in order to obtain the desired surface characteristics.

The present invention provides a block-shaped measuring chamber unit comprising differently oriented surface parts and a plurality of separate shallow chamber-forming depressions formed in said surface parts, at least one of said depressions being formed in each of said surface parts, respectively, each of said depressions having a fluid inlet and a separate fluid outlet, said fluid inlets and outlets being formed solely as straight passages in said unit, and comprising straight passages each interconnecting two of said depressions and being oblique to the surface parts in which said two depressions are formed. It is understood that such a measuring chamber unit may relatively easily be made from a block-shaped body of glass, stainless steel, or another material having suitable characteristics. Thus, the shallow depressions in the differently orientated surface parts may be made by milling, grinding or other suitable machining, and each of the straight passages or bores each interconnecting two depressions or extending between a depression and the outer surface of the block-shaped unit, may be made by a simple drilling operation. Due to the simple shape of the measuring chamber unit according to the invention the walls of the depressions and the straight passages or bores may in a relatively simple manner be given the finish desired by grinding, polishing or in another suitable manner. Furthermore, the arrangement of the measuring chamber depressions in differently orientated surface parts of the block-shaped body makes it possible to obtain a measuring apparatus of a more compact structure than in case all measuring chambers are arranged at the same side of the block-shaped body, and due to the fact that the passages or bores forming inlets and outlets of the measuring chambers are straight they may easier be kept clean so that the possibilities of avoiding contamination of a sample on which measurements are being made, with substances originating from a preceding sample, are substantially improved.

The said depressions may be formed in oppositely directed surface parts, and the depressions in one surface part may then be laterally offset from each depression in the opposite surface part. The depressions may, alternatively, be formed in non-parallel surface parts of which adjacent surface parts may define an acute, but preferably define an obtuse angle therebetween.

The depressions in the block-shaped unit or body may for example be interconnected in such a manner that three or more interconnecting passages extend from a centrally arranged depression in one surface part to a corresponding number of depressions formed in an opposite surface part or adjacent surface parts of the unit. However, according to the invention all of the depressions in the block-shaped unit are preferably connected in series by means of the straight bores or passages, and the cross-sectional area of each of the straight passages is preferably substantially smaller than the area of each of said depressions. Furthermore, each of the straight passages preferably opens in the peripheral zones of the depressions. Thus the depressions and the interconnecting passages or bores may together form a continuous measuring passage which may have a relatively uniform cross-sectional area throughout its length without sudden changes of direction, and due to the fact that the interconnecting bores open into the peripheral zones or rim zones of the depressions it is possible to obtain an advantageous flow pattern without formation of "pockets" when a fluid sample is passed through the measuring passage.

The said depressions functioning as measuring chambers must, of course, be closed in one way or another. This may advantageously be done by means of the measuring instrument associated with each single measuring chamber. This measuring instrument may, for example, be an electrochemical measuring electrode of the type having a semi-permeable membrane at one end. The measuring electrode may then continuously be mounted on the block-shaped unit or body in such a manner that the end of the measuring electrode provided with the membrane faces the depression and seals the same outwardly, possibly also by use of a sealing ring or another suitable sealing element.

In order to make accurate measurements it is often necessary to secure that the fluid sample on which measurements are being made is retained at a predetermined temperature. It may therefore be necessary to supply heat to or remove heat from a fluid sample within the measuring chamber unit, and for that reason it may be desirable to make the block-shaped body from a material having good heat conductive characteristics. This requirement is fulfilled by stainless steel and other metals. However, by certain measurements errors may arise when the measuring chamber is defined by an electrically conductive material, and therefore, in practice one has been reduced to use glass or plastic. Of these materials the first mentioned has several very good characteristics. However, it is relatively difficult to machine and finish. The last mentioned material which is easy to shape and finish has some less desirable characteristics as mentioned above, and plastic also has a relatively poor heat conductivity. According to the invention the block-shaped body may advantageously be made from machinable glass-ceramic. This material which is available in the form of blocks and in qualities showing a very good machinability, has proved to possess other characteristics making it at least as suitable for measuring chamber units of the type in question as glass.

According to another aspect the invention comprises any shape of a measuring chamber unit for use in connection with electrochemical measuring apparatuses, especially apparatuses for measuring on very small amounts of blood or other body fluids, said measuring unit being at least partly made from machinable glass-ceramic. This material has proved to have surprisingly good characteristics in connection with this special use irrespective of the shape of the measuring chamber unit and of whether said unit defines one or more measuring chambers.

In the present specification the term "block-shaped unit" or "block-shaped body" is intended to comprise not only a parallelepiped shaped body, but any body having differently orientated plane or curved surface parts in which said depressions may be formed.

BRIEF DESCRIPTION OF THE DRAWING

The invention will now be described more in detail with reference to the diagrammatic drawing wherein.

DESCRIPTION OF THE PREFERRED EMBODIMENTS

Figure 1:
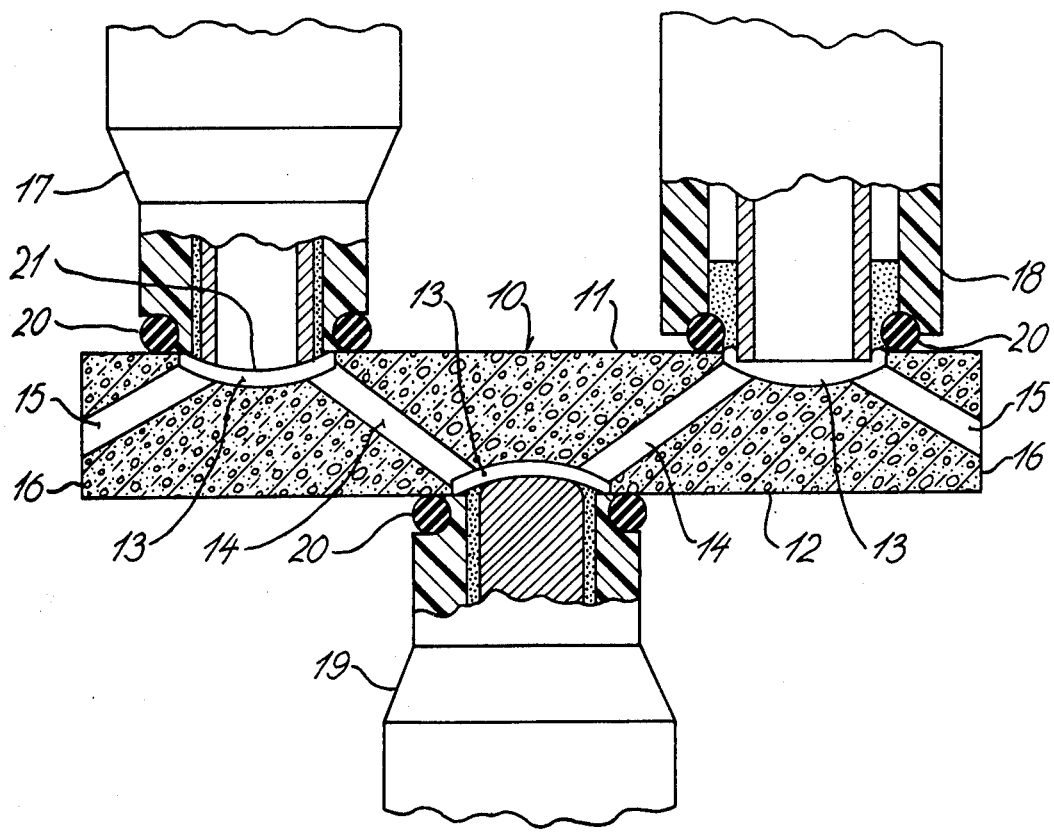
FIG. 1 is a side view and partial sectional view of an embodiment of the measuring chamber unit according to the invention provided with measuring instruments.

FIG. 1 shows a measuring chamber unit consisting of a block 10 which may be made from glass, a suitable metal such as stainless steel, or another suitable material. The said unit is, however, preferably made from machinable glass-ceramic, for example of the type marketed under the trade mark MACOR by Corning Glass Works, Corning, New York, U.S.A. Such glass-ceramic has a partially-crystalline structure which enables it to be machined to precise tolerances with ordinary metal working tools and equipment. The block 10 has two opposite side surfaces 11 and 12 in which a plurality—in the present case three—shallow depressions 13 are formed. In the longitudinal direction of the block 10 these depressions are arranged offset in relation to each other, and they are connected in series by means of obliquely extending, straight passages or bores 14 which preferably open into the peripheral zones of the depressions. Straight passages or bores 15 extend from the depressions adjacent to the end surfaces 16 of the block 10 and open into these end surfaces.

A number of measuring instruments or measuring electrodes 17, 18, and 19 are positioned in such a manner that each measuring electrode closes and seals a corresponding one of the depressions 13 outwardly whereby a measuring chamber is defined therein. As clearly shown in the drawing the measuring chambers defined by the depressions 13 form together with the bores 14 and 15 a continuous, slightly zigzag-shaped measuring passage. The measuring electrodes 17–19 are secured in relation to the block 10 in any suitable manner, not shown, and by means of sealing rings 20, for example O-rings, the necessary sealing between the electrodes 17–19 and the adjacent surface parts of the block 10 may be obtained. These sealing rings 20 may simultaneously be used for retaining a semi-permeable membrane 21 stretched over the end of the electrode.

Figure 2:
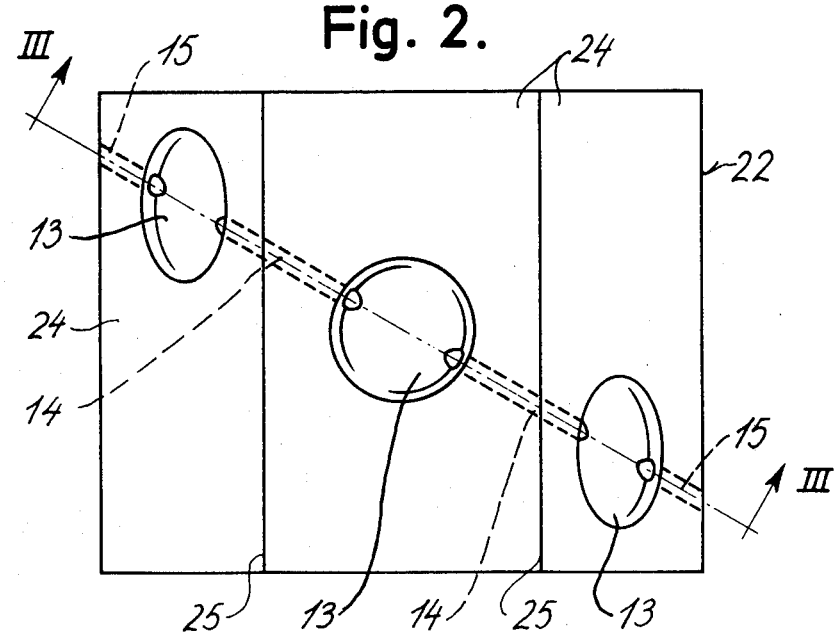
FIG. 2 is a plan view of a second embodiment of the measuring chamber unit according to the invention.
Figure 3:
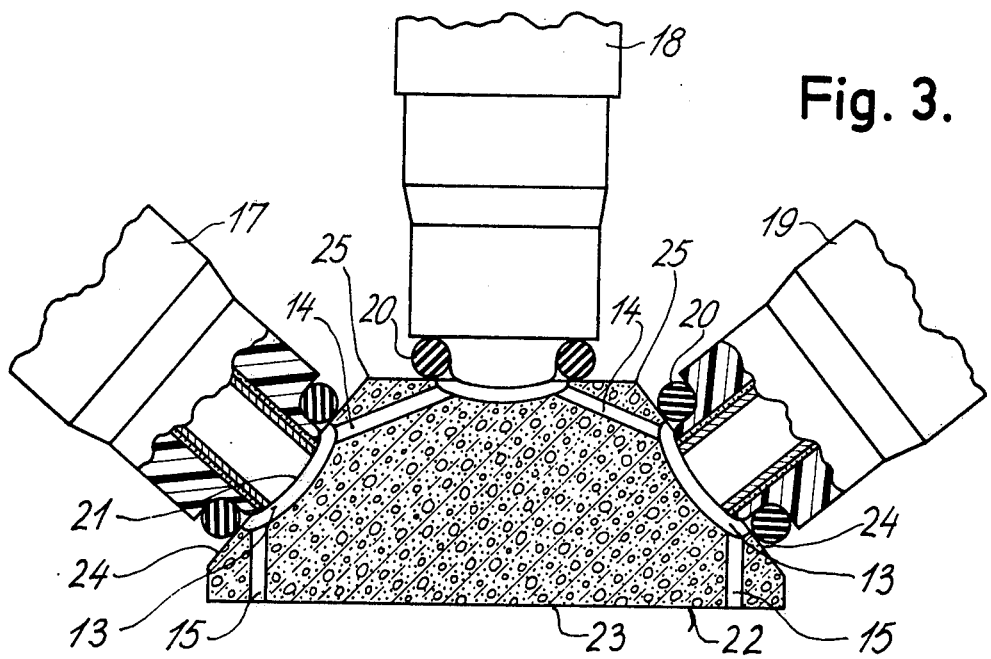
FIG. 3 is a sectional view along the line III—III of the embodiment shown in FIG. 2 provided with measuring instruments.
Figure 4:
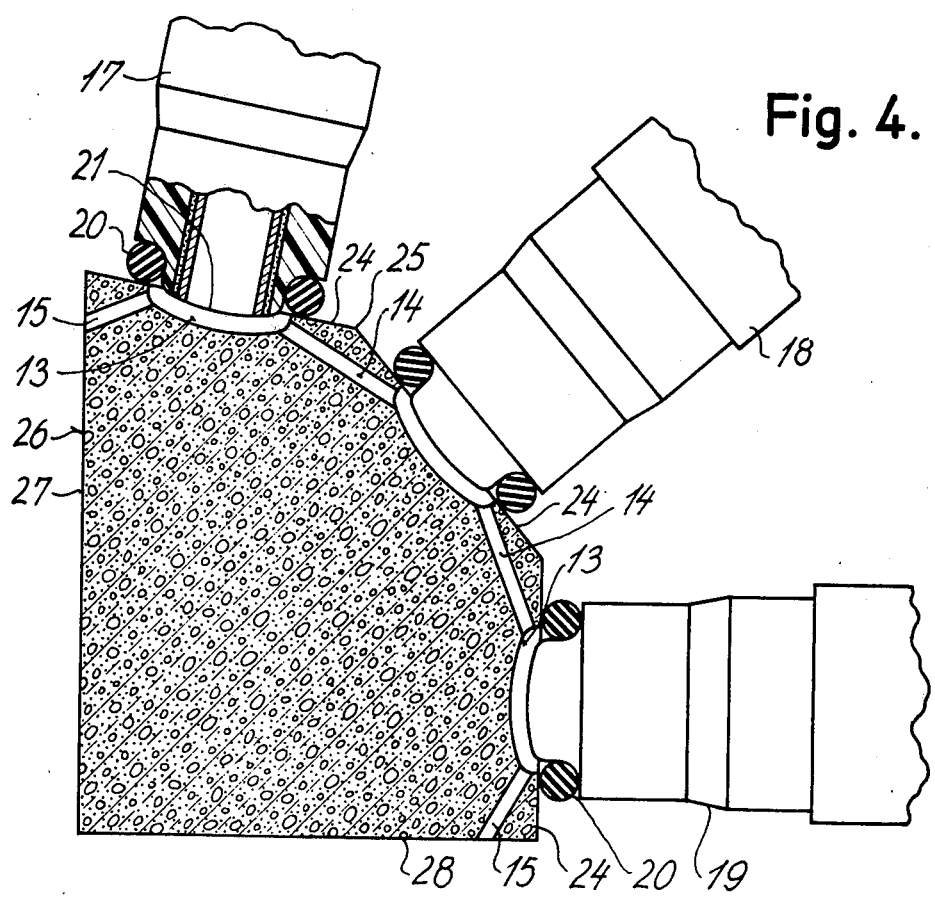
FIG. 4 is a sectional view corresponding to that shown in FIG. 3, but in a modified embodiment.

FIGS. 2–4 show further embodiments of the measuring chamber unit according to the invention, and in these figures elements corresponding to those shown in FIG. 1 have been provided with like reference numerals.

FIGS. 2 and 3 show a measuring chamber unit formed by a block 22 having a bottom surface 23 and upper surface parts 24. A shallow depression 13 is formed in each of the surface parts 24 and arranged laterally offset as shown in FIG. 2. Adjacent surface parts 24 form obtuse-angled corners or edges 25, and the straight passages or bores 14 connecting the depressions 13 in series extend obliquely to the surface parts 24 as shown in FIG. 3. The inlet and outlet passages or bores 15 open into the bottom surface 22 and extend at right angles thereto but obliquely to the adjacent surface parts 24.

FIG. 4 shows an embodiment including a block 26 having a shape somewhat different from that of the blocks shown in FIGS. 1–3. The block 26 has surfaces 27 and 28 extending at right angles in relation to each other and surface parts 24 in which the shallow depressions 13 are formed. Adjacent surface parts 24 define obtuse-angled corners or edges 25, and the bores or passages 14 interconnecting the depressions 13 are oblique to the adjacent surface parts 24. The inlet and outlet passages 15 open into the surfaces 27 and 28, respectively.

In the embodiments shown the bottom wall of each depression has a shape corresponding substantially to the shape of the membrane of the associated measuring instrument, and the membrane is spaced from the bottom surface of the depression at a small distance which is substantially of the same order as the diameter of the passages or bores 14 and 15.

Any of the measuring chamber units disclosed may be used in a measuring apparatus of the automatic or semi-automatic type, for example of the type disclosed in U.S. Pat. No. 3,874,058. When the measuring chamber unit is included in such an apparatus for measuring a blood sample the measuring electrodes 17, 18, and 19 may, for example, be intended for measuring partial pressure of $CO_2$, pH-value, and partial pressure of $O_2$, respectively. Such measuring electrodes are well known in the art and, therefore, the measuring electrodes shown on the drawings will not be further described.

It should be understood that various changes and modifications of the embodiments shown on the drawings may be made within the scope of this invention. Thus, the blocks 10, 22 and 26 need not necessarily have a polygonal cross-sectional shape, but could, for example, have slightly curved outer surface parts or be shaped as a cylinder. Even though the measuring chambers are advantageously defined in the depressions 13 by means of the measuring instruments or measuring electrodes 17–19 in the manner shown on the drawings, it should be understood that the measuring chambers might alternatively be defined in any other manner, for example by means of plates or apparatus parts which engage the surrounding surface part of the block 10 and in which the measuring instruments may be mounted.

As mentioned above it has been found that glass-ceramic has surprising advantages when used in connection with measuring chambers of the above type, especially for use in measuring blood and other body liquids. Therefore, the present invention also comprises any use of the material glass-ceramic for such measuring chambers irrespective of their form and shape.

We claim:

1. A block-shaped measuring chamber unit, especially for use in electrochemical measuring apparatus, comprising differently orientated surface parts and a plurality of separate, shallow chamber-forming depressions formed in said surface parts, at least one of said depressions being formed in each of said surface parts, respectively, each of said depressions having a fluid inlet and a separate fluid outlet, said fluid inlets and outlets being formed solely as straight passages in said unit, and comprising straight passages each interconnecting two of said depressions and being oblique to the surface parts in which said two depressions are formed.

2. A measuring chamber unit according to claim 1, wherein the cross-sectional area of each of said straight passages is substantially smaller than the area of each of said depressions.

3. A measuring chamber unit according to claim 2, wherein said depressions are formed in oppositely directed surface parts, a said depression in one surface part being laterally offset from each depression in the opposite surface part.

4. A measuring chamber unit according to claim 3, wherein said depressions are connected in series with one another by said straight passages.

5. A measuring chamber unit according to claim 2, wherein said depressions are formed in non-parallel surface parts.

6. A measuring chamber unit according to claim 5, wherein each said straight interconnecting passage interconnects depressions formed in adjacent surface parts defining an obtuse angle therebetween.

7. A measuring chamber unit according to claim 6, wherein said depressions are connected in series with one another by said straight passages.

8. A measuring chamber unit according to claim 2, wherein said straight passages open into the peripheral zones of said depressions.

9. A measuring chamber unit according to claim 2, wherein said unit is at least partly made from machinable glass-ceramic.

10. A block-shaped measuring chamber unit for use in electrochemical measuring apparatus and made from machinable glass-ceramic, said unit comprising first and second substantially flat surfaces defining an obtuse angle therebetween, a shallow chamber-forming depression formed in each of said surfaces, said depressions being interconnected by a straight passage being oblique to said flat surfaces, said first depression further being connected to a straight inlet passage and said second depression further being connected to a straight outlet passage formed in said block.

11. A measuring chamber unit according to claim 10, wherein said straight passages open into the peripheral zones of said depressions.

12. A measuring chamber unit according to claim 11, wherein the cross-sectional area of each of said straight passages is substantially smaller than the area of each of said depressions in said flat surfaces.

13. An electrochemical measuring apparatus comprising a block-shaped measuring chamber unit having differently orientated surface parts and a plurality of separate, shallow chamber-forming depressions formed in said surface parts, at least one of said depressions being formed in each of said surface parts, respectively, each of said depressions having a fluid inlet and a separate fluid outlet, said fluid inlets and outlets being formed solely as straight passages in said unit, and comprising straight passages each interconnecting two of said depressions and being oblique to the surface parts in which said two depressions are formed, and measuring instruments sealed to said unit and closing said depressions respectively to form chambers.

14. An electrochemical measuring apparatus according to claim 13, wherein each of said instruments extends outwardly substantially vertical to the respective surface part.

* * * * *